United States Patent [19]
Lenz et al.

[11] Patent Number: 5,690,623
[45] Date of Patent: Nov. 25, 1997

[54] VENTED OSTOMY POUCH WITH PROTECTED GAS FILTER

[75] Inventors: Morten Lenz, Rungsted; Steen Holmberg, Helsingor, both of Denmark

[73] Assignee: Dansac A/S, Fredensborg, Denmark

[21] Appl. No.: 782,216

[22] Filed: Jan. 13, 1997

[51] Int. Cl.⁶ .................................................. A61F 5/44
[52] U.S. Cl. ......................... 604/333; 604/332; 604/342
[58] Field of Search .................................... 604/332–345

[56] References Cited

U.S. PATENT DOCUMENTS

| | | | |
|---|---|---|---|
| 4,387,712 | 6/1983 | Briggs et al. | 604/333 |
| 4,411,659 | 10/1983 | Jensen et al. | 604/332 |
| 4,723,951 | 2/1988 | Steer | 604/333 |
| 5,250,042 | 10/1993 | Torgalkar et al. | 604/333 |

FOREIGN PATENT DOCUMENTS

| | | |
|---|---|---|
| 2149306 | 6/1985 | United Kingdom . |
| 2177301 | 1/1987 | United Kingdom . |

*Primary Examiner*—Robert A. Clarke
*Attorney, Agent, or Firm*—Tilton Fallon Lungmus

[57] ABSTRACT

Vented ostomy pouches are disclosed in which a first wall is securable to a patient's peristomal skin surfaces and the obverse second wall is provided with an outlet opening for the escape of gases from the pouch. A deodorizing gas filter extends over the outlet and a third wall, or internal barrier wall, is located within the pouch and divides it into two chambers. The barrier wall operates to block the passage of solids and most liquids from the first chamber to the second but is provided with at least one vent that permits the flow of gases into the second chamber from the first. A filter-protecting panel in the second chamber directs such gases along a circuitous route as they travel from the vent to the outlet. A connection, preferably in the form of a spot weld, joins the barrier wall to the bodyside first wall of the pouch at about the elevation of the filter to prevent the barrier wall from blocking against other surfaces and obstructing the flow of gases through the vent and filter.

18 Claims, 2 Drawing Sheets

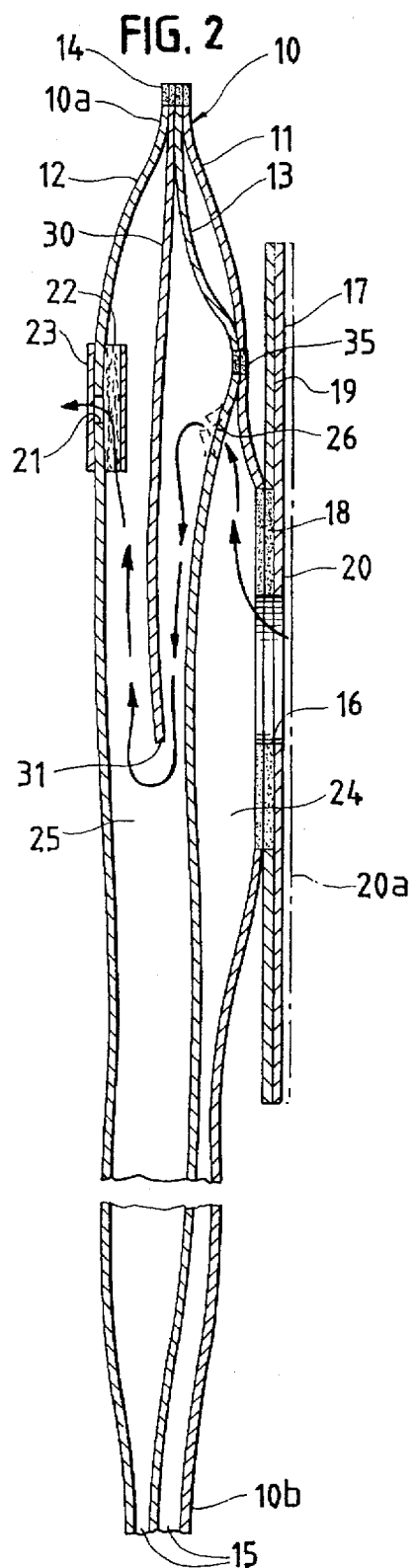
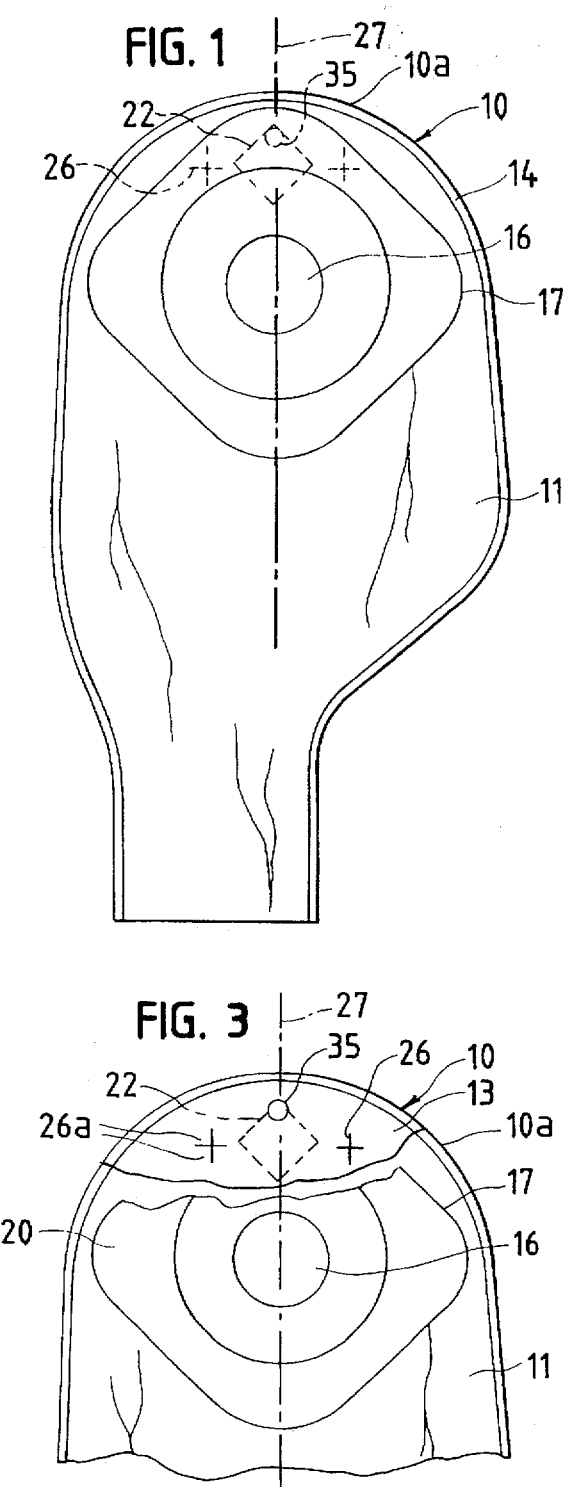

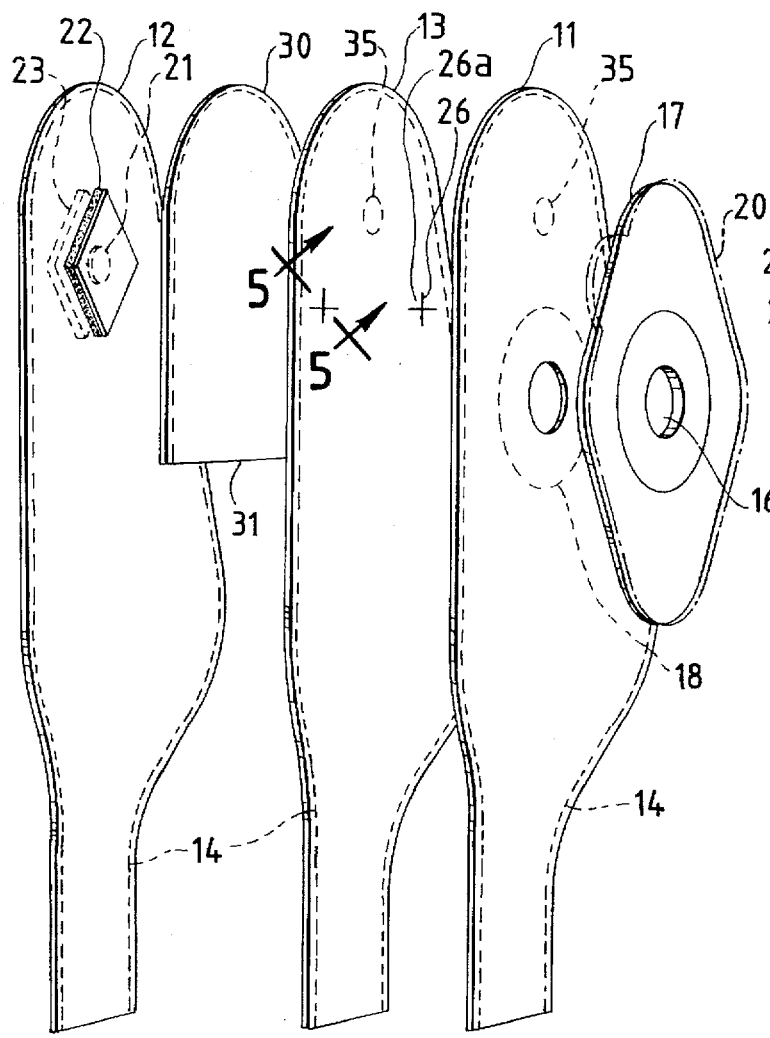
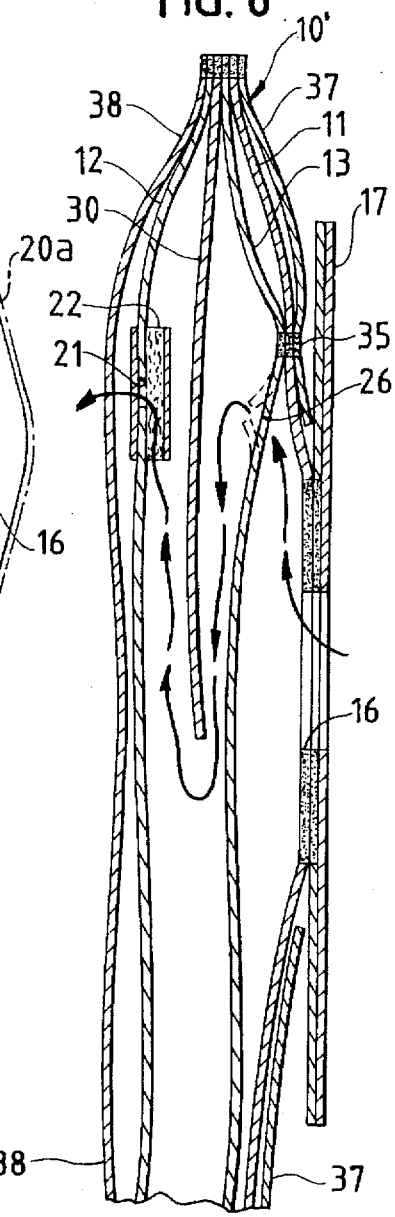
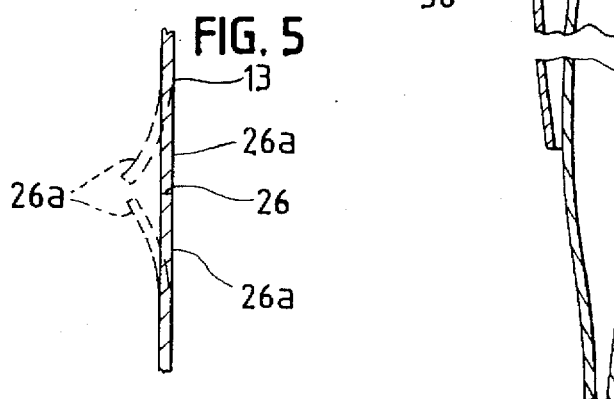

VENTED OSTOMY POUCH WITH PROTECTED GAS FILTER

BACKGROUND AND SUMMARY

Jensen et al U.S. Pat. No. 4,411,659 discloses an ostomy pouch having an apertured intermediate film designed to protect a filter from contact with and possible obstruction by exudate. To keep the intermediate film from blocking against the front wall of the pouch during use, surface areas of the intermediate film are raised or embossed. Other patents and published applications, such as Torgalkar et al U.S. Pat. No. 5,250,042, Steer U.S. Pat. No. 4,723,951, Craig Medical GB 2,177,301A, and Craig Medical GB 2,149,306A also disclose ostomy pouches with filter-protecting intermediate films.

In practice, not all pouches with filter-protecting intermediate films work as intended because, among other things, small amounts of liquid may still pass through the apertures in the intermediate films and interfere with filter operation, even to the point of blocking the flow of gases through such a filter. Also, at least in pouch constructions that do not utilize embossed film, moisture in the second chamber in which the filter is located may promote a blocking effect between the intermediate film and the inside surface of the pouch wall about the filter, or about the aperture in the intermediate film, thereby obstructing the flow of gases intended to pass through the filter and exit the pouch.

Accordingly, a main aspect of this invention lies in providing an ostomy pouch, particularly an ileostomy pouch, in which a deodorizing gas filter is protected against contact with and clogging by liquids (also solids) contained in the pouch, and in which the means for so protecting the filter does not itself become an obstruction to the flow of gases through and out of the pouch.

Briefly, a pouch embodying the invention has first and second walls of thermoplastic film sealed to each other along their outer edges with the first wall having a stoma-receiving opening and being externally provided with attachment means about that opening for securing the pouch to a wearer. The obverse second wall has a gas outlet opening provided with a gas filter for deodorizing gases exiting the pouch. Within the pouch is a third wall, or internal barrier wall, of thermoplastic film that divides the pouch into adjacent first and second chambers. The barrier wall has at least one gas vent, and preferably at least two such gas vents in laterally-spaced symetrical relation, located above the stoma-receiving opening for the flow of gases from one chamber to the other.

The pouch also includes a filter-protecting panel of thermoplastic film located in the upper portion of the second chamber between the gas vent of the barrier wall and the filter-equipped outlet opening of the second wall. The panel has its side and top edges sealed to the outer edges of the other walls but has its unsecured lower edge spaced above the lower end of the pouch. Connecting means, preferably in the form of a spot weld, joins together the first wall and barrier wall of the pouch at a point of connection located well above the lower limits of the filter-protecting panel. Most advantageously, the spot weld is located above the vent (or vents) in the barrier wall and in general alignment with the deodorizing gas filter of the second wall.

As the pouch receives stomal discharge, causing the outer walls to spread apart, the spot connection between the first wall and the barrier wall causes the barrier wall in the area of the weld to move in a direction away from the second wall (and away from the filter-protecting panel) at the same time that gases, liquids, and/or solids entering the first chamber of the pouch through the stoma opening tend to inflate or expand that chamber. As a result, the venting means in the barrier wall, located above the stoma opening and below the spot weld, is unobstructed by the first wall, or by the filter-protecting panel in the second chamber, and allows flatus gases to pass from the first chamber into the second chamber and then out through the deodorizing gas filter at the outlet opening of the pouch.

Each vent in the barrier wall of the pouch takes the form of one or more flap-providing slits. Particularly effective results are achieved by forming each vent with a pair of slit crossed at right angles in an "x" pattern. The four triangular flaps of the vent readily open to allow the passage of gas but otherwise tend to assume closed positions in the absence of a pressure differential between the first and second chambers of the pouch.

The pouch may include soft fabric covering layers on one or both sides of the pouch to enhance wearer comfort and prevent the outer surfaces of the first and second walls from sticking to the skin or to clothing. Such a covering layer may be formed from a soft, non-woven thermoplastic material, in which case the covering layer extending over the first wall of the pouch may be joined to that wall not only by the peripheral heat seal but also by the same spot weld that joins the first wall and the third or barrier wall together.

Other features, advantages and objects of the invention will become apparent from the specification and drawings.

DRAWINGS

FIG. 1 is a rear plan view of an ostomy pouch embodying the invention.

FIG. 2 is an enlarged and somewhat schematic vertical sectional view of the pouch.

FIG. 3 is a fragmentary rear plan view of the pouch with the attachment means (wafer) cut away to reveal the spot weld joining the first wall (bodyside wall) and third wall (barrier wall).

FIG. 4 is an exploded perspective view.

FIG. 5 is a greatly enlarged sectional view taken along line 5–5 of FIG. 4 and illustrating details of the flap construction and operation.

FIG. 6 is a somewhat schematic vertical sectional view similar to FIG. 2 but depicting a second embodiment of the invention.

DETAILED DESCRIPTION OF PREFERRED EMBODIMENTS

Referring to the drawings, and particularly to the embodiment depicted in FIGS. 1–5, the numeral 10 generally designates an ostomy pouch which, in a normal state of orientation (i.e., with a wearer in an upright position), has upper and lower ends 10a and 10b, respectively. The pouch includes a first wall 11, which may also be referred to as a rear or bodyside wall, a second wall 12, also referred to as an obverse or front wall, and a third wall 13 also referred to as an internal barrier wall. The three walls are of the same size and outline, and are all formed from a suitable gas and liquid impervious thermoplastic film such as, for example, a polyolefin film laminated with an appropriate barrier material. One suitable commercially-available material comprises low density polyethylene coextruded with a layer of polyvinylidene chloride. Such material is available under the designation "Saranex" from Dow Chemical Company, Midland, Mich.

Some or all of the peripheral outer edges of the three walls may be heat-sealed together as indicated by numeral 14 in FIG. 2. In the embodiment illustrated, only the top and side edges are sealed together, the pouch being open at its bottom and being of the drainable type generally preferred for ileostomy use. The drain openings 15 at the tapered lower end of the pouch would, in use, be closed by a suitable clamping device such as the closure shown and described in Nolan U.S. Pat. No. 3,523,534 or Morrison U.S. Pat. No. 5,125,133. Alternatively, the pouch might be provided at its lower end with a valved drain assembly such as disclosed in Jensen U.S. Pat. No. 4,280,498.

The first or bodyside wall 11 of the pouch is provided with a stoma-receiving opening 16 surrounded by attachment means 17 for use in securing the pouch to a patient. The attachment means might take the form of a coupling ring for detachably joining the pouch to the mating ring of an adhesive patch or faceplate as disclosed, for example, in Lavender U.S. Pat. No. 5,185,008. In the construction illustrated, the attachment means instead takes the form of an adhesive wafer or faceplate that is permanently secured by annular heat seal 18 to wall 11 about stoma-receiving opening 16. The wafer is essentially composed of two layers: a flexible pouchside layer 19 of thermoplastic film or fabric, and an adhesive layer 20 which may be any of a variety of pressure-sensitive adhesive materials such as medical-grade acrylic adhesives or hydrocolloid-containing adhesive compositions that are skinfriendly and have both wet and dry tack. A removable release sheet 20a, shown only in phantom in FIGS. 2 and 4, covers the adhesive surface and is peeled away by the user at the time of application.

The second or front wall 12 has a gas outlet opening 21 positioned well above the location of stoma-receiving opening 16. A flat pad-like deodorizing gas filter 22 is secured to the inside surface of wall 12 over opening 21 so as to deodorize gases exiting the pouch through the opening. The filter may be made of charcoal cloth and have a construction similar to that disclosed in Nolan et al U.S. Pat. No. 3,759,260. Since flatus deodorizing gas filters are well known, and since the particular construction of filter 22 is not part of this invention, a description of the details of construction and operation are believed unnecessary herein. It should be noted, however, that to prevent the filter from being contacted by external fluids (as, for example, when the pouch is worn while a patient takes a shower), and to prevent leakage of liquid from the pouch in any case, a patch 23 of a semipermeable hydrophobic material, such as semipermeable polytetrafluoroethylene, may be secured to the outside surface of wall 12 over opening 21.

The third or barrier wall 13 divides the interior of the pouch into two chambers: a first or rear chamber 24 and a second or front chamber 25. Venting means are provided for the passage of gases from the first chamber to the second. As shown most clearly in FIG. 4, such means takes the form of a pair of laterally-spaced vents 26 located in the upper portion of wall 13 above the location of the stoma-receiving opening 16 in bodyside wall 11. More specifically, the vents are spaced horizontally apart on opposite sides, and at equal distances from, the vertical midline 27 of the pouch's upper portion (FIG. 1). Preferably, the vents are located at approximately the same elevation as filter 22. (In FIG. 2, the venting means is illustrated schematically as a single vent directly above stoma opening 16 only for clarity in illustrating the directions of gas flow through the pouch.) While the provision of two vents is believed particularly advantageous, a greater number might be provided or, alternatively, a single vent might be used.

Each vent 26 takes the form of a pair of slits crossing at right angles to define four converging triangular flaps 26a. The flaps are normally coplanar with wall 13 but flex forwardly into open positions as shown in FIG. 5 when the pressure within chamber 24 exceeds that of chamber 25.

A filter-protecting panel 30 is located in the upper portion of the second chamber 25 between walls 12 and 13. The panel may be formed of the same material as walls 11–13 and has its side and top edges secured to the other walls by the same heat seal 14 that joins the edges of the other walls. It will be noted, however, that the panel 30 has a free lower edge 31 located at or slightly below the level of stoma-receiving opening 16. Gases passing into the second chamber through vents 26 must therefore travel downwardly and then upwardly to reach filter 22 and outlet 21. Any liquids traveling into the second chamber through the vents is therefore directed downwardly and is not likely to reverse direction and reach the filter and outlet opening. While the filter-protecting panel 30 might conceivably be omitted in some applications, its presence is considered particularly important where the vents 26 in the barrier wall 13 are at essentially at the same elevation, and are therefore in close proximity to, filter 22 and outlet 21.

An important feature of the pouch lies in the point of connection between the third wall (or barrier wall) 13 and the bodyside first wall 11. Referring to FIGS. 2–4, walls 11 and 13 are joined together by a small spot weld 35 located along vertical midline 27 well above stomal opening 16 and also above the level of vents 26. (In the exploded view of FIG. 4, the areas of heat seals between the walls of the pouch are indicated by broken lines.)

The spot weld has the effect of causing localized rearwardly-directed forces to be applied to the barrier wall 13 in the vicinity of vents 26 at the same time that other forces are being applied to walls 13 and 11 by gases, liquids and/or solids entering the first chamber to expand that chamber. As a result, the barrier wall 13 in the area of vents 26 tends to be pulled away from filter-protecting panel 30 (where provided) and away from wall 12 in the vicinity of filter 22. It has also been found that the point of connection keeps walls 11 and 13 from blocking together when the pouch is empty and promotes separation of the walls, thereby exposing vents 26 to incoming gases, as materials are discharged from the stoma into the pouch. Additionally, the spot weld eliminates or reduces the possibility that wall 13 might block against panel 30 (or against wall 12 in the absence of panel 30), thereby preventing the flaps 26a from opening to permit the flow of gases from the first chamber into the second chamber through the vents.

The result is a collection pouch in which flatus may flow through freely from stoma-receiving opening 16 to the pouch's outlet opening 21 along a circuitous route indicated by arrows 36 in FIG. 2 while, at the same time, filter 22 is protected by the barrier wall 13, and by panel 30, from contact with liquid (also solids) that might otherwise interfere with, and even completely obstruct, the filtering of gases and the discharge of such gases from the pouch.

The embodiment depicted in FIG. 6 differs from the embodiment also described in only one respect: it includes covering layers 37 and 38 over the outer surfaces of walls 11 and 12 to enhance wearer comfort and avoid the possibility that exposed outer surfaces of walls 11 and 12 might stick or cling to skin surfaces and clothing. Layers 37 and 38 are formed from any suitable thermoplastic fabric, such as a non-woven fabric composed of thermoplastic fibers, capable of being heat sealed to the remainder of the pouch by peripheral heat seal 14 and spot weld 35.

In FIG. 6, the covering layers are provided on both sides of the pouch; however, in certain applications, it may be desirable to provide such a covering layer along only one side of the pouch, such as the side facing the wearer's body.

While in the foregoing, embodiments of the invention have been disclosed in considerable detail for purposes of illustration, it will be understood by those skilled in the art that many of these details may be varied without departing from the spirit and scope of the invention.

We claim:

1. An ostomy pouch having upper and lower ends and comprising first and second walls of thermoplastic film sealed to each other along their outer edges; said first wall having a stoma-receiving opening and being externally provided with attachment means extending about said opening for securing said pouch to a wearer; said second wall being provided with a gas outlet opening and having a deodorizing gas filter secured thereto over said outlet opening for deodorizing gases passing therethrough; a third wall of thermoplastic film interposed between said first and second walls and having outer edges heat sealed to said outer edges of said first and second walls for dividing said pouch into adjacent first and second chambers; said third wall having at least one gas vent located above said stoma-receiving opening for the flow of gases from one chamber to the other; wherein the improvement comprises connecting means joining said first and third walls together at a point of connection spaced below the upper end of said pouch and above said gas vent.

2. The pouch of claim 1 in which said connecting means comprises a spot weld joining said first and third walls together at said point of connection.

3. The pouch of claim 2 in which said spot weld is located along a vertical midline of said pouch extending from said upper end downwardly below said stoma-receiving opening.

4. The pouch of claim 3 in which at least two of said gas vents are provided in said third wall and are located on opposite sides of said vertical midline below said spot weld.

5. The pouch of claims 1, 2 or 3 in which said pouch includes at least one outer covering layer of soft non-woven heat-sealable material; said covering layer having substantially the same outline as said first and second walls and having edge portions heat sealed to the remainder of said pouch by the same heat seal joining said first, second and third walls together.

6. The pouch of claim 5 in which said non-woven covering layer extends over said first wall and is joined thereto by said connecting means.

7. The pouch of claim 6 in which said pouch includes a second outer covering layer of soft non-woven heat-sealable material; said second covering layer covering said second wall and having edge portions heat sealed thereto by the same heat seal joining said first, second and third walls together.

8. The pouch of claim 1 in which said gas vent comprises at least one flap-providing slit in said third wall; said flap of said gas vent being normally closed in the absence of a pressure differential between said chambers.

9. The pouch of claim 8 in which said vent comprises a pair of slits intersecting each other at substantially right angles and defining four flaps of generally triangular shape.

10. An ostomy pouch having upper and lower ends and comprising first and second walls of thermoplastic film sealed to each other along their outer edges; said first wall having a stoma-receiving opening and being externally provided with attachment means extending about said opening for securing said pouch to a wearer; said second wall being provided with a gas outlet opening and having a deodorizing gas filter secured thereto over said outlet opening for deodorizing gases passing therethrough; a third wall of thermoplastic film interposed between said first and second walls and having outer edges heat sealed to said outer edges of said first and second walls for dividing said pouch into adjacent first and second chambers; said third wall having gas venting means located above said stoma-receiving opening for the flow of gases from one chamber to the other; wherein the improvement comprises a filter-protecting panel of thermoplastic film located in the upper portion of said second chamber between said gas vent and said outlet opening and having side and top edges positioned between and heat sealed to said outer edges of said second and third walls; said panel having a lower edge unsecured to said second and third walls; and connecting means joining said first and third walls together at a point of connection spaced below the upper end of said pouch and located above said lower edge of said panel.

11. The pouch of claim 10 in which said connecting means comprises a spot weld joining said first and third walls at said point of connection.

12. The pouch of claim 11 in which said spot weld is located along said pouch's vertical midline above the level of said gas venting means.

13. The pouch of claim 12 in which said gas venting means comprises at least two vents in said third wall located on opposite sides of said vertical midline below said spot weld.

14. The pouch of claims 10, 11 or 12 in which said pouch includes at least one outer covering layer of soft non-woven heat-sealable material; said covering layer being of substantially the same outline as said first, second and third walls and having edge portions heat sealed to the remainder of said pouch by the same heat seal joining said first, second and third walls together.

15. The pouch of claim 14 in which said non-woven covering layer extends over said first wall and is also joined thereto by said connecting means.

16. The pouch of claim 15 in which said pouch includes a second outer covering layer of soft non-woven heat-sealable material; said second covering layer covering said second wall and having edge portions heat sealed thereto by the same heat seal joining said first, second and third walls together.

17. The pouch of claim 10 in which said venting means comprises at least one flap-providing slit in said third wall; said flap being normally closed in the absence of a pressure differential between said chambers.

18. The pouch of claim 17 in which said venting means comprises a pair of straight slits in said third wall intersecting each other at substantially right angles to define four flaps of generally triangular shape.

* * * * *